(12) United States Patent
Joziak et al.

(10) Patent No.: US 8,568,697 B2
(45) Date of Patent: Oct. 29, 2013

(54) HIGH FLUORIDE ION RECOVERY COMPOSITIONS

(75) Inventors: Marilou Joziak, South River, NJ (US); Jason Nesta, Cedar Knolls, NJ (US)

(73) Assignee: Colgate-Palmolive Company, New York, NY (US)

( * ) Notice: Subject to any disclaimer, the term of this patent is extended or adjusted under 35 U.S.C. 154(b) by 1040 days.

(21) Appl. No.: 12/053,233

(22) Filed: Mar. 21, 2008

(65) Prior Publication Data

US 2009/0238777 A1 Sep. 24, 2009

(51) Int. Cl.
| | | |
|---|---|---|
| *A61K 8/21* | (2006.01) | |
| *A61K 8/00* | (2006.01) | |
| *A61Q 11/00* | (2006.01) | |

(52) U.S. Cl.
USPC ............ 424/52; 424/49; 433/215; 433/216

(58) Field of Classification Search
USPC ............... 424/49, 52; 433/215, 216
See application file for complete search history.

(56) References Cited

U.S. PATENT DOCUMENTS

| | | | |
|---|---|---|---|
| 3,538,230 A | 11/1970 | Pader at al. | |
| 3,689,637 A | 9/1972 | Pader | |
| 3,711,604 A | 1/1973 | Colodney et al. | |
| 3,863,006 A | 1/1975 | Hodosh | |
| 3,911,104 A | 10/1975 | Harrison | |
| 3,935,306 A | 1/1976 | Roberts et al. | |
| 4,040,858 A | 8/1977 | Wason | |
| 4,631,185 A | 12/1986 | Kim | |
| 4,751,072 A | 6/1988 | Kim | |
| 4,774,077 A | 9/1988 | Ferlauto, Jr. et al. | |
| 4,897,269 A | 1/1990 | Mezei | |
| 4,925,654 A | 5/1990 | Gaffar | |
| 5,071,637 A | 12/1991 | Pellico | |
| 5,240,697 A * | 8/1993 | Norfleet et al. ............... | 424/52 |
| 5,334,375 A | 8/1994 | Nabi et al. | |
| 5,496,558 A | 3/1996 | Napolitano et al. | |
| 6,159,459 A | 12/2000 | Hunter et al. | |
| 6,379,654 B1 | 4/2002 | Gebreselassie et al. | |
| 7,198,779 B2 | 4/2007 | Rifa Pinol et al. | |
| 7,402,416 B2 | 7/2008 | Szeles et al. | |
| 2003/0157033 A1 * | 8/2003 | Endo ............................ | 424/49 |
| 2004/0022747 A1 * | 2/2004 | Fisher et al. ................. | 424/52 |
| 2007/0092600 A1 | 4/2007 | Miyai | |
| 2008/0003187 A1 | 1/2008 | Joziak et al. | |

FOREIGN PATENT DOCUMENTS

| | | |
|---|---|---|
| CN | 1788714 | 6/2006 |
| EP | 0 525 913 A | 2/1993 |
| EP | 0525913 | 2/1993 |
| EP | 1 149 534 A | 10/2001 |
| EP | 1437126 | 7/2004 |
| FR | 920 324 A | 4/1947 |
| FR | 1 426 869 A | 2/1966 |
| FR | 2341302 | 9/1977 |
| FR | 2 755 010 A | 4/1998 |
| JP | H05-194166 | 8/1993 |
| JP | 2001-506307 | 5/2001 |
| JP | 2001-520191 | 10/2001 |
| JP | 2009-542705 | 12/2009 |
| WO | WO 95/01154 | 1/1995 |
| WO | WO 99/63959 | 12/1999 |
| WO | WO 02/26203 | 4/2002 |
| WO | WO 02/074274 | 9/2002 |
| WO | WO 03/039503 | 5/2003 |
| WO | WO 2004/019802 | 3/2004 |
| WO | WO 2006/013081 | 2/2006 |
| WO | 2008005688 A | 1/2008 |
| WO | WO 2008/145475 | 12/2008 |
| WO | WO 2009/099455 | 8/2009 |

OTHER PUBLICATIONS

International Search Report PCT/US2009/037782 mailed Aug. 6, 2009.
International Search Report and Written Opinion in International Application No. PCT/US2009/037777, mailed Oct. 9, 2009.
Malaya Meditsinskaya Entsiklopediya, T. 2, M., Sovietskaya entsiklopediya, 1991, p. 569 (middle column of document). English translation submitted herewith.
Soderling, et al., 1998, "Betaine-containing toothpaste relieves subjective symptoms of dry mouth", Acta Odontologica Scandinavica, Oslo, vol. 56, pp. 65-69.
Ward, F.M., Ph.D, 2007, "Stabilizers, Naturally", retrieved from the Internet on Feb. 27, 2012 at <URL: http://www.foodproductdesign.com/articles/2007/10/stabilizers-naturally.aspx>.
Xanthan Gum, Jungbunzlauer, 2006, Chapters: Properties. Compatibility. Retrieved from the Internet on Feb. 27, 2012, at <URL: http://www.jungbunzlauer.com/media/uploads/pdf/Xanthan_Gum/Xanthan_Gum_2006.pdf>.

\* cited by examiner

*Primary Examiner* — Lezah Roberts
(74) *Attorney, Agent, or Firm* — Howard C. Lee

(57) ABSTRACT

Compositions having high fluoride ion recovery comprising a hydrocolloid, a heteropolysaccharide, a PVME/MA copolymer, and a fluoride ion source and use thereof, e.g., in the treatment of xerostomia and/or sensitive teeth.

16 Claims, No Drawings

HIGH FLUORIDE ION RECOVERY COMPOSITIONS

BACKGROUND OF THE INVENTION

Dental caries is a major dental disease that affects the majority of the population. In the early part of the 20$^{th}$ century, investigators discovered that fluoride was effective in reducing the incidence of caries. Since that time, fluoride research has developed, and it is now well accepted that fluoride treatments benefit dental health.

Most dentifrice compositions contain fluoride ions in the range of 1,000 to 1,500 ppm. However, for some segments of the population, higher amounts of fluoride may be even more beneficial. Some patients often suffer from either aggressive caries, or are otherwise at a higher risk of dental decay than the general population. Other patients suffer from xerostomia, or tooth sensitivity. These patients may benefit from special dentifrices that incorporate high levels of fluoride ions. For example, some such dentifrices incorporate sodium fluoride as a fluoride ion source, in amounts of over 1,500 ppm, such as around 2,000 ppm or around 5,000 ppm.

However, it may be difficult to maintain the effective properties of high levels of fluoride in oral care compositions. Fluoride ion sources may have low solubility, fluoride ions may precipitate out of a dentifrice composition and fluoride ions may react with other ingredients in a dentifrice composition. On the other hand, if more solvent is added to the composition to increase fluoride ion availability, the composition changes and tends to lose the desirable physical characteristics associated with an acceptable dentifrice, e.g., the viscosity of the compositions may be too thin and runny.

The use of mucoadhesive polymers in combination with fluoride is known in the art. However, ionic salts, including fluoride ions known to interact and become entrapped in multiple polymers, causes a reduction of available fluoride ions. Additionally, typical toothpaste compositions containing mucoadhesive polymers may experience undesirable "stickiness" or "tackiness" in the mouth following use.

Thus, there is a need in the art for a high-fluoride content oral care compositions, e.g., for patients who need high levels of fluoride, e.g., those suffering from xerostomia and/or tooth sensitivity. It is further desirable to develop such a composition in which the anticaries activity of the fluoride ion is maintained successfully over time. It is also desirable to develop compositions which do not result in a sticky or tacky sensation following use, and provides a smooth feel during and after brushing.

BRIEF SUMMARY OF THE INVENTION

The present invention is based on the surprising discovery that fluoride ion availability is maintained in high level fluoride compositions comprising a hydrocolloid, heteropolysaccharide, and a polyvinylmethylether/maleic anhydride (PVME/MA) copolymer. One aspect of the present invention is directed to compositions which provide greater than 90% fluoride recovery, e.g., greater than 95% fluoride recovery.

The present invention includes composition 1.0, a dentifrice composition comprising a hydrocolloid, a heteropolysaccharide, and a PVME/MA copolymer.

Additional compositions of the present invention include compositions:

1.1 Composition 1.0 comprising a fluoride ion source sufficient to provide from about 1,000 ppm to about 25,000 ppm fluoride ions;

1.2 Composition 1.0 or 1.1 comprising a fluoride ion source to provide at least about 4,000 ppm of fluoride ions, e.g. about 4500 ppm, about 5000 ppm, or about 5500 ppm.

1.3 Any of the preceding compositions wherein the hydrocolloid is selected from Arabic gum, xanthan gum, agar, carrageenan gum, guar gum, dextran, geletain, or combinations thereof;

1.4 Any of the preceding compositions comprising xanthan gum;

1.5 Any of the preceding compositions comprising from about 0.05% to about 5% hydrocolloid, e.g., about 0.1% to about 4%, about 0.2% to about 3%, about 0.5%, 0.6%, 0.7%, 0.8%, or 0.9%;

1.6 Any of the preceding compositions wherein the heteropolysaccharide is pectin;

1.7 Any of the preceding compositions comprising from about 0.01% to about 4% heteropolysaccharide, e.g., from about 0.05% to about 3%, about 0.08%, about 0.1%, or about 0.12%;

1.8 Any of the preceding compositions comprising from about 0.1% to about 10% of a PVME/MA copolymer, e.g., from about 0.2% to about 5%, from about 0.5% to about 2%, about 0.5%, about 1%, or about 2%;

1.9 Any of the preceding compositions which provides a high fluoride ion recovery;

1.10 Any of the preceding compositions comprising an effective amount of an antibacterial agent;

1.11 Any of the preceding compositions comprising a halogenated diphenyl ether, e.g., triclosan:

1.12 Any of the preceding compositions comprising an effective amount of a desensitizing agent;

1.13 Any of the preceding compositions comprising a potassium salt, capsaicin, eugenol, a strontium salt, a zinc salt, a chloride salt, or combinations thereof;

1.14 Any of the preceding compositions comprising potassium nitrate, potassium bicarbonate, potassium chloride, potassium citrate, potassium oxalate, or combinations thereof;

1.15 Any of the preceding compositions wherein the fluoride ion source is present in an amount of about 0.5% to about 5% by weight;

1.16 Any of the preceding compositions wherein the fluoride ion source is sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluoride, or combinations thereof;

1.17 Any of the preceding compositions comprising at least about 40% by weight water;

1.18 Any of the preceding compositions comprising stannous ion agent, triclosan, triclosan monophosphate, chlorhexidine, alexidine, hexetidine, sanguinarine, benzalkonium chloride, salicylanilide, arginate esters, ethyl lauryl arginate, bisphenols domiphen bromide, tetradecylpyridinium chloride, N-tetradecyl-4-ethylpyridinium chloride, octenidine, delmopinol, octapinol, nisin, zinc ion agent, copper ion agent, essential oils, furanones, bacteriocins, a basic amino acid, or combinations thereof;

1.19 Any of the preceding compositions comprising an abrasive silica, an amorphous silica, a humectant, a stabilizing agent, an antibacterial agent, a sweetener, a surfactant, or combinations thereof;

1.20 Any of the preceding compositions substantially free of polyethylene glycol;
1.21 Any of the preceding compositions which is a dentifrice, e.g., a toothpaste;
1.22 Any of the preceding compositions which provides a high recovery of fluoride ions;
1.23 Composition 1.21 having from about 95% to about 120% fluoride ion recovery;
1.24 Composition 1.21 having about 100% fluoride ion recovery;
1.25 Compositions 1.22 or 1.23 wherein the fluoride ion recovery is 3, 6, 9, or 12 months following manufacture of the compositions.

The present invention is also directed to a method for treating xerostomia and/or tooth sensitivity comprising applying any one of compositions 1.0-1.25 to the oral cavity. e.g., by brushing.

The present invention is also directed to the use of any one of compositions 1.0-1.22 to maintain high fluoride recovery in a dentifrice composition.

DETAILED DESCRIPTION OF THE INVENTION

Throughout the present disclosure, ranges are used as a shorthand for describing each and every value that is within the range. Any value within the range can be selected as the terminus of the range.

The compositions of the present invention contain an orally acceptable polyvinylmethylether/maleic anhydride (PVME/MA) copolymer. The PVME/MA copolymer is present from about 0.1% to about 20%, for example about 0.5% to about 10% by weight. Generally the methyl vinyl ether to maleic anhydride ratio in the copolymer is about 1:4 to about 4:1, and the copolymer has an average molecular weight of about 30,000 to about 1,000,000, for example about 30,000 to about 500,000. Preferred PVME/MA copolymers include those under the GANTREZ brand from ISP (Wayne, N.J.). The PVME/MA copolymer may also act as an antibacterial enhancing agent if present in an antibacterial enhancing effective amount.

The compositions of the present invention also include a hydrocolloid, which may serve as an emulsifying, thickening and/or gelling agent, and is one that can further contribute to maintaining the anticaries activity of the fluoride ion over time. Preferred hydrocolloids include plant exudates such as gum Arabic; seaweed extracts such as xanthan gum, agar and carrageenan gum; plant seed gums or mucilages such as guar gum; cereal gums such as starches; fermentation gums such as dextran; animal products such as gelatin; or combinations of any of these hydrocolloids. A preferred hydrocolloid is xanthan gum.

The compositions of the present invention also include a heteropolysaccharide, e.g., derived from plant cell walls. The heteropolysaccharide may be esterified. e.g., partially methyl esterified, and may serve as an emulsifying, thickening, and/or gelling agent. A preferred heteropolysaccharide is pectin. A preferred pectin may be obtained from CP Kelco (San Diego, Calif.) under the tradename GENU® pectin USP/100.

The compositions of the present invention are able to provide a high recovery of fluoride ions. Generally, the compositions are able to provide high fluoride ion recovery of from about 90% to about 120%, e.g., about 90% to about 110%, about 95% to about 110%, or about 100%. The terms "fluoride ion recovery," "recovery of fluoride ions" and the like describes the relationship between the theoretical amounts fluoride ions available in a composition, and the actual available amounts of fluoride ion present when a composition is manufactured, or at any given time afterwards, e.g., 1 week, 1 month, 2 months, 3 months, 6 months, or 1 year following manufacturing. "High" fluoride ion recovery means that the actual amounts of available fluoride ions are about 90% or greater than the theoretical amounts of available fluoride ions in the composition, e.g., about 95% or greater. Indeed, high fluoride recovery may also mean that the actual amounts of available fluoride ions are greater than 100% of the theoretical amounts of available fluoride ions. e.g., from about 100% to about 120%, e.g., about 100% to about 110%, or about 105%. The actual amount of fluoride ion availability may be determined based on ionic fluoride testing involving an ion specific electrode for fluoride, as well as nuclear magnetic resonance imaging. Such techniques are known by those of skill in the art, and may be performed in accordance with standard procedures known and accepted in the art. Methods of calculating theoretical amounts of fluoride ions are also known in the art, and may depend on a number of factors including the selection of a particular fluoride ion source, and solvents utilized in the composition.

Fluoride ions may be provided by a fluoride ion source. A fluoride ion source may be anything that is capable of releasing fluoride ion in an aqueous environment. Typical sources include soluble salts of the fluoride ion; such as, for example: sodium fluoride, potassium fluoride, calcium fluoride, zinc fluoride, zinc ammonium fluoride, lithium fluoride, ammonium fluoride, stannous fluoride, stannous fluorozirconate, and complex fluorides, monofluorophosphates and salts thereof such as, e.g., sodium monofluorophosphate or potassium monofluorophosphate, laurylamine hydrofluoride, diethylaminoethyloctoylamide hydro fluoride, didecyldimethylammonium fluoride, cetylpyridinium fluoride, dilaurylmorpholinium fluoride, sarcosine stannous fluoride, glycine potassium fluoride, glycine hydrofluoride, and amine fluorides. See, e.g., U.S. Pat. Nos. 3,538,230, 3,689,637, 3,711, 604, 3,911,104, 3,935,306 and 4,040,858, the contents of which are herein incorporated by reference in their entirety.

The fluoride ion source is most preferably in an amount such that it is capable of maintaining a high level of fluoride ion in the composition that is at least about 5,000 ppm, and in some instances up to as much as 25,000 ppm. Preferably, the fluoride ions are present in an amount of at least about 5,000 ppm. In order to provide such a concentration in the optimal ppm range, the exact weight percentage of the fluoride ion source in the composition may vary, depending upon the stoichiometric properties of different fluoride ion sources. Preferably, the amount of fluoride ions present in the composition is such that the composition is capable of providing high fluoride ion recovery 3 or 6 months following manufacture of the composition, preferably, 100% fluoride ion recovery after 3 or 6 months following manufacture of the composition. It may also be found that the compositions of the present invention maintain fluoride ion availability following storage, e.g., after 3 or 6 months, compared to the fluoride ion content when the compositions is initially prepared.

The compositions of the present invention may comprise a quantity of water that is higher than that normally associated with a traditional oral care compositions. The hydrocolloid, heteropolysaccharide and PVEME/MA copolymer forms a paste that traps the water in the formulation to achieve a desired rheology, while maintaining a high concentration of fluoride ions in the composition.

The oral care composition is preferably in the form of a dentifrice. Preferred dentifrices include but are not limited to various types of toothpaste, tooth polish, tooth gel, mouthwash and mouth rinse, denture adhesive or cream or the like.

In one embodiment, an oral care composition is provided that can incorporate high levels of fluoride for anticaries treatment, tooth sensitivity, and xerostomia. The compositions may also incorporate one or more sensitivity treatment agents, e.g., potassium salts such as potassium nitrate, potassium bicarbonate, potassium chloride, potassium citrate, and potassium oxalate; capsaicin: eugenol; strontium salts; zinc salts; chloride salts and combinations thereof. Such agents may be added in effective amounts, which preferably vary between about 0.01% to about 10% by weight based on the total weight of the composition, depending on the agent chosen.

Preferably, a desensitizing agent is a potassium salt in an amount of at least about 5% by weight of a potassium salt based on the total weight of the composition. Most preferably, the composition includes about 504 to about 10% by weight of the potassium salt. Effective amounts of such potassium salts and their use are described in e.g., the following patents: U.S. Pat. Nos. 3,863,006, 4,631,185 and 4,751,072, the contents of which are incorporated by reference in their entirety. Most preferably, the desensitizing agent is potassium nitrate.

The oral care compositions of the present invention preferably further include at least about 40% by weight water based on total weight of the composition, e.g., at least 50%, or about 40% to about 60% by weight water. This is typically more water than would be used in a standard sensitive tooth or anticaries dentifrice such as toothpaste, because one of ordinary skill in the art would expect a larger amount of water to yield a composition that is highly liquid.

Other thickening agents that may be used in the oral care compositions of the present invention. Other thickening agents are known in the art, and include, but are not limited to: silica thickeners; glycerites; sodium alginate; carboxymethyl cellulose; hydroxyethyl cellulose, hydroxypropyl cellulose; hydroxymethyl cellulose; hydroxymethyl carboxypropyl cellulose; methyl cellulose; ethyl cellulose; sulfated cellulose; as well as mixtures and combinations of these compounds. Such additional thickeners may be used in amounts of up to about 15 wt % of the composition based on the total weight of the composition.

The compositions of the present invention may also include a variety of common additional active agents typically used in oral care formulations, including but not limited to: triclosan; triclosan monophosphate; chlorhexidine; alexidine; hexetidine; sanguinarine; benzalkonium chloride; salicylanilide; arginate esters; ethyl lauryl arginate, bisphenols, domiphen bromide; tetradecylpyridinium chloride; N-tetradecyl-4-ethylpyridinium chloride; octenidine; delmopinol; octapinol; nisin; zinc ion agent; copper ion agent; essential oils, furanones; bacteriocins; salts of the foregoing active agents and mixtures and combinations thereof.

Optional additives for the oral care compositions of the present invention may also be used, such as those commonly used for forming a dentifrice, including but not limited to: abrasives and/or amorphous silica, humectants, stabilizing agents, antibacterial agents, sweeteners, colorants, surfactants, healing agents, other caries preventative agents, chelating/sequestering agents, vitamins, amino acids, proteins, anti-plaque agents, anti-calculus agents, opacifiers, antibiotics, anti-enzymes, enzymes, pH control agents, oxidizing agents, antioxidants, whitening agents and preservatives.

One or more abrasive or polishing materials may also be included in the oral care compositions of the present invention. The abrasive or polishing material can be any material that is acceptable for use in a dentifrice, does not excessively abrade dentin and is compatible with the other components of the oral care composition. Exemplary abrasive or polishing materials include, but are not limited to: silicas, aluminas, phosphates, carbonates, and mixtures, derivatives and salts thereof, and resinous abrasive materials.

One or more humectants may be added to the oral care compositions of the present invention, for providing body or texture to the formulations and for maintaining moisture in the formulations. Useful humectants include, but are not limited to: various polymeric glycols and other hydroxy-based humectants such as, e.g., propylene glycols, glycerol, erythritol, xylitol, sorbitol, mannitol, lactitol, hydrogenated starch hydrolyzates and combinations of these components. The compositions of the present invention may also be substantially free of polyethylene glycol. e.g., less than 1%, less than 0.5%, or 0% or about 0% by weight of the composition.

Antibacterial agents can be used if reduction of microorganisms is desired, and can include known antibacterial agents used in dentifrice formulations such as, e.g., benzoic acid, sodium benzoate, potassium benzoate, boric acid, and phenolic compounds such as betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride and cetylpyridinium bromide. Compositions of the present invention may also include one or more basic amino acids, e.g., arginine, in free base or salt form.

Sweeteners may be used in the oral care compositions of the present invention if desired, and may include any of those commonly used in a dentifrice to impart a pleasing taste to the product. Suitable sweeteners include but are not limited to: saccharins and derivatives thereof, cyclamates and derivatives thereof, acesulfane-K, thaumatin, neohisperidin dihydrochalcone, ammoniated glycyrrhizin, dextrose, levulose, sucrose, mannose, glucose and any other suitable sweeteners.

One or more surfactants may also be included in the oral care compositions of the present invention. Surfactants useful for the oral care formulations of the present invention include, e.g., anionic surfactants, zwitterionic surfactants, nonionic surfactants, amphoteric surfactants, and cationic surfactants. A preferred surfactant is cocoamidopropyl betaine.

One of skill in the art would recognize that an ingredient may serve various purposes in the composition. For example, polyethylene glycol may act as a thickening agent, viscosity modifier, surfactant, and/or humectant in a dentifrice composition.

The other ingredients noted may be any of those commonly used in dentifrice formulations and can be selected based upon the intended end use of the formulations and to optimize the physical and aesthetic characteristics of the formulations.

The invention will now be described with respect to the following non-limiting examples:

EXAMPLE 1

Five dentifrice compositions formulated to achieve a theoretical available fluoride ion concentration of 5,000 ppm are prepared. The ingredients for the compositions are presented in Table 1

TABLE 1

|  | X | A | B | C | D |
|---|---|---|---|---|---|
| Poloxamer 407 | 1.5 |  | 1.5 | 1.5 | 1.5 |
| Glycerin | 3 | 12 |  | 3 | 3 |
| Polyethylene glycol |  | 3 | 3 |  |  |
| Xanthan gum | 0.7 | 0.5 | 0.2 | .7 |  |

TABLE 1-continued

|  | X | A | B | C | D |
|---|---|---|---|---|---|
| Pectin | 0.1 | 0.1 |  |  | 0.1 |
| Hydroxy ethyl cellulose |  | 0.1 | 0.2 |  |  |
| Carbopol 974 |  |  | 0.2 |  |  |
| Propylene glycol | 5 | 5 |  |  | 5 |
| Sorbitol | 17.5 | 8.8 | 23.9 | 17.6 | 17.5 |
| Gantrez S-97 (PVME/MA copolymer) | 1 |  |  | 1 | 1 |
| Water | 48.1 | 48.7 | 52 | 48.2 | 48.8 |
| Sodium fluoride | 1.1 | 1.1 | 1.1 | 1.1 | 1.1 |
| Sodium saccharin | 0.4 | 0.4 | 0.4 | 0.4 | 0.4 |
| Sodium benzoate | 0.5 | 0.5 | 0.5 | 0.5 | 0.5 |
| Potassium sorbate | 0.1 | 0.1 |  | 0.1 | 0.1 |
| Cetylpyridinium chloride | 0.2 |  |  | 0.2 | 0.2 |
| Dibasic potassium phosphate | 2 | 2 | 1.2 | 2 | 2 |
| Sodium hydroxide | 0.5 |  |  | 0.5 | 0.5 |
| Polyoxyl 40 hydrogenated castor oil | 3 | 3 | 3 | 3 | 3 |
| Zeodent 165 | 6 | 4.5 | 3 | 6 | 6 |
| Zeodent 114 | 8 | 8 | 8 | 8 | 8 |
| Cocoamidopropyl betaine | 0.3 |  | 0.3 | 0.3 | 0.3 |
| Flavor | 1 | 1 | 1 | 1 | 1 |
| Sodium methyl cocoyl taurate |  | 1.2 | 0.5 |  |  |
| FD&C Blue #1 | trace | trace | Trace | Trace | trace |

Compositions X, A, and B formed a paste suitable as a toothpaste. Composition C is found to form a paste suitable as a toothpaste. Composition D is found to not form a paste useful as a dentifrice composition.

EXAMPLE 2

Compositions X, A and B was used by volunteers and found to have a "smooth" feeling. Composition C would be found by volunteers to have a "smooth" feeling in the oral cavity following use of the composition.

EXAMPLE 3

Compositions X, A, B and C was tested for fluoride ion availability when the compositions are initially prepared, after 3 months of accelerated aging (at 40° C. and 75% relative humidity), and after 6 months of accelerated aging. Results are provided in Table 2.

TABLE 2

| Composition | Initial fluoride ion in ppm (% recovery) | 3 month fluoride recovery in ppm (% recovery) | 6 month fluoride ion recovery in ppm (% recovery) |
|---|---|---|---|
| X | 5088 (102%) | 5071 (101%) | 5157 (103%) |
| A | 4354 (87%) | N/A | N/A |
| B | 4705 (94%) | 4545 (91%) | 4345 (87%) |
| C | 4400 (88%) | N/A | N/A |

Results showed that compositions lacking xanthan gum, pectin, and a PVME/MA copolymer immediately suffer loss of fluoride ion availability. The initial fluoride ion availability following manufacturing is unacceptable (below 90%) for Compositions A and C; thus, aging studies are not performed on Compositions A and C. Composition B continued to lose available fluoride ion over time. Surprisingly, Composition X maintains full and complete available fluoride amounts, even following 6 months of aging.

It will be appreciated by those skilled in the art that changes and alterations may be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A dentifrice composition comprising:
   a) a hydrocolloid;
   b) pectin;
   c) a polyvinylmethylether/maleic anhydride (PVME/MA) copolymer; and
   d) a fluoride ion source sufficient to provide from about 5,000 ppm to about 25,000 ppm available fluoride ions; wherein the composition provides a 90% or greater fluoride ion recovery 6 months following manufacture.

2. The composition of claim 1 wherein the hydrocolloid is selected from the group consisting of Arabic gum, xanthan gum, agar, carrageenan gum, guar gum, dextran, gelatin, and combinations thereof.

3. The composition of claim 1 wherein the hydrocolloid is xanthan gum.

4. The composition of claim 1 comprising from about 0.05% to about 5% hydrocolloid.

5. The composition of claim 1 comprising from about 0.01% to about 4% of pectin.

6. The composition of claim 1 comprising from about 0.1% to about 10% of a PVME/MA copolymer.

7. The composition of claim 1 further comprising an effective amount of an antibacterial agent.

8. The composition of claim 7 wherein the antibacterial agent is selected from the group consisting of a halogenated diphenyl ether, cetylpyridinium chloride, and combinations thereof.

9. The composition of claim 1 further comprising an effective amount of a desensitizing agent.

10. The composition of claim 9 wherein the desensitizing agent is selected from the group consisting of a potassium salt, capsaicin, eugenol, a strontium salt, a zinc salt, a chloride salt, and combinations thereof.

11. The composition of claim 1 wherein the fluoride ion source is selected from the group consisting of sodium fluoride, potassium fluoride, calcium fluoride, zinc fluoride, zinc ammonium fluoride, lithium fluoride, ammonium fluoride, stannous fluoride, stannous fluorozirconate, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides, and combinations thereof.

12. The composition of claim 1 further comprising a stannous ion agent, triclosan, triclosan monophosphate, chlorhexidine, alexidine, hexetidine, sanguinarine, benzalkonium chloride, salicylanilide, arginate esters, ethyl lauryl arginate, bisphenols, domiphen bromide, tetradecylpyridinium chloride, N-tetradecyl-4-ethylpyridinium chloride, octenidine, delmopinol, octapinol, nisin, zinc ion agent, copper ion agent, essential oils, furanones, bacteriocins, a basic amino acid, or combinations thereof.

13. The composition of claim 1 further comprising silica, a humectant, a stabilizing agent, an antibacterial agent, a sweetener, a surfactant, or combinations thereof.

14. The composition of claim 1 which is a toothpaste.

15. A method for treating xerostomia and/or tooth sensitivity comprising applying the composition of claim 1 to an oral cavity.

16. The method of claim 15 wherein the composition is applied to the oral cavity by brushing of the teeth.

* * * * *